(12) United States Patent
Kashefi Khorasani (10) Patent No.: US 9,566,376 B2
(45) Date of Patent: Feb. 14, 2017

(54) APPARATUS FOR EXCHANGING MASS- AND/OR BETWEEN TWO FLUIDS

(76) Inventor: Ahmad Ali Kashefi Khorasani, Aachen (DE)

(*) Notice: Subject to any disclaimer, the term of this patent is extended or adjusted under 35 U.S.C. 154(b) by 502 days.

(21) Appl. No.: 14/122,436

(22) PCT Filed: May 31, 2011

(86) PCT No.: PCT/EP2011/002681
§ 371 (c)(1),
(2), (4) Date: Jan. 21, 2014

(87) PCT Pub. No.: WO2012/163372
PCT Pub. Date: Dec. 6, 2012

(65) Prior Publication Data
US 2014/0154137 A1 Jun. 5, 2014

(51) Int. Cl.
A61M 37/00 (2006.01)
A61M 1/16 (2006.01)
B01D 61/28 (2006.01)
B01D 63/02 (2006.01)
A61M 1/26 (2006.01)
A61M 1/10 (2006.01)

(52) U.S. Cl.
CPC ............ *A61M 1/1698* (2013.01); *A61M 1/10* (2013.01); *A61M 1/1006* (2014.02); *A61M 1/267* (2014.02); *B01D 61/28* (2013.01); *B01D 63/02* (2013.01); *A61M 1/106* (2013.01); *A61M 2240/00* (2013.01); *B01D 2313/20* (2013.01); *B01D 2313/243* (2013.01); *B01D 2313/90* (2013.01)

(58) Field of Classification Search
CPC .. A61M 1/1698; A61M 1/1006; A61M 1/267; A61M 1/10; B01D 61/28; B01D 63/02
USPC .............................. 604/4.01–6.14; 422/44–48
See application file for complete search history.

(56) References Cited

U.S. PATENT DOCUMENTS 8,398,858 B2  3/2013  Kaschefi-Khorasani
2002/0143397 A1  10/2002  vonSegesser

FOREIGN PATENT DOCUMENTS

DE  102020005135 A  7/2011
WO  2009110652 A  9/2009

*Primary Examiner* — Philip R Wiest
(74) *Attorney, Agent, or Firm* — Andrew Wilford (57) ABSTRACT

The invention relates to an apparatus and a process for mass- and/or energy-transfer between two media, in particular between blood and a gas/gas mixture, having a chamber (1) through which a first medium, in particular blood, flows and in which a bundle of mass- and/or energy-permeable hollow fibers through which the second medium can flow and around which the first medium can flow is arranged transverse to the flow direction of the first medium, in which the chamber (1) is configured as an elastic shell (3) at least in a region which completely surrounds the bundle, where a rigid housing (6) is arranged around the elastic shell (3) and the inner wall of the housing contacts the shell (3) in a plurality of first regions (9) and the inner wall of the housing is not in contact with and is in particular at a spacing from the shell (3) in at least one second region (10), preferably a plurality of second regions (10) in the direction of the extension of the hollow fibers, where the one hollow space or at least one of the plurality of hollow spaces formed in the second regions (10) between shell (3) and housing (6) joins a fluid connection (11) passing through the wall of the housing.

17 Claims, 3 Drawing Sheets

APPARATUS FOR EXCHANGING MASS- AND/OR BETWEEN TWO FLUIDS

CROSS REFERENCE TO RELATED APPLICATIONS

This application is the US-national stage of PCT application PCT/EP2011/002681 filed 31 May 2011 and claiming the priority of PCT patent application PCT/EP2011/002681 itself filed 31 May 2011.

The invention relates to an apparatus for exchanging mass and/or energy between two fluids, particularly between blood and a gas/gas mixture (or water, if a pumping module is the heat exchanger of the apparatus) with a chamber through which the first fluid, particularly blood, flows and through which, particularly perpendicular to the flow direction of the first fluid, extends a bundle of mass- and/or energy-permeable hollow fibers through which the second fluid can flow and through which the first fluid cannot flow. The invention also relates a process for operating such an apparatus.

Such apparatuses can be used to exchange mass and/or energy between a first and a second fluid. The hollow fibers in the above-mentioned chamber are sealed with respect to the chamber such that the first fluid can flow through the chamber without being able to come into direct contact with the second fluid flowing flows through the hollow fibers. The mass and/or energy transfer between the two fluids therefore takes place through the permeable hollow fibers.

It is known in the prior art, for example, that the bundle of hollow fibers can be longitudinally tubular in a longitudinally extending chamber, with connections at the axial ends of the chamber each in fluid communication with the plurality of axial end openings of the hollow fibers at the respective axial end of the bundle.

In a preferred application, such apparatuses can be used, for example, in medical technology, for example in blood purification techniques such as dialysis, blood separation or even as artificial lungs, and thus as so-called oxygenators.

In this application, the blood can be regarded as the first fluid and oxygen as the second fluid that is conducted through the individual hollow fibers of the above-described bundle. $CO_2$-enriched blood can then be delivered through the chamber, and as a result of the different partial pressures of oxygen and $CO_2$ on the two sides of the mass- and/or energy-permeable hollow fibers of the bundle, a mass transfer occurs such that $CO_2$ is removed from the blood and the blood is enriched with oxygen from the hollow fibers. In this application, the hollow fibers are therefore $CO_2$- and $O_2$-permeable. Such an apparatus can act as an artificial lung and therefore take over a patient's lung function in part or even completely. In other, particularly medical applications, the hollow fibers can also be permeable to other substances.

In order to pump the first fluid through the chamber, external pumps are usually required with such an apparatus. In the area of medicine, particularly in the case of oxygenators, to which the present invention is not limited, however, this means that, in addition to the conventional apparatuses known up to now in the prior art, an external pump must be provided with which blood is pumped out of the patient's body, through the apparatus and then back into the patient's body. The patient can be either a human or animal.

The external use of pumps results in the problem that a substantial portion of the pumped blood volume is taken up by the pump, since it must be completely filled with blood in order for the apparatus to function (large extracorporeal volume=thinning of the blood). Consequently, conventional apparatuses are hardly or only to a limited extent usable with infants or premature babies or even in very small animals, since the blood volume can be less than 100 milliliters in these cases, but the volume of pumps is usually in this order of magnitude or even larger, which necessitates the use of additional blood plasma or plasma replacement or blood replacement or erythrocyte concentrate when treating infants or premature babies or small animals, which can place a heavy burden on the organism.

External pumps, such as peristaltic pumps, for example, present another problem, particularly at low (blood) flow rates as a result of the very uniform path (serpentine blood movement within the oxygenator), since this results in a very uniform blood flow that is less favorable for oxygen enrichment. Furthermore, areas of stagnation can occur with the associated danger of coagulation (and complement) and finally the failure of the oxygenator, for example as a result of the clotting of the blood in the oxygenator. This problem can also occur in a similar manner with other first and second fluids.

It is therefore the object of the invention to provide an apparatus of the general type described above as well as a process in which a sufficient pump function can be made available with as little volume of the first fluid as possible, particularly as little blood volume as possible, particularly in order to enable use of an apparatus according to the invention in infants and premature babies. Another aim of such a small construction of an apparatus according to the invention is that it can also be implanted in a patient. It is another object of the invention to achieve highly effective mass transfer.

It should also be noted in this context that blood is cited as the first fluid and oxygen as the second fluid, for example, in the description of an embodiment of the apparatus, the described embodiment shall be deemed as having been disclosed for any first and second fluid.

According to the invention, this object is achieved by forming the chamber as an elastic shell at least where it completely surrounds the bundle of hollow fibers, particularly that forms a complete enclosure at one or more planes spaced axially one after the other and extending perpendicular to the hollow fibers, a rigid housing around the elastic shell having an inner wall engaging the shell in several first regions and out of contact, for example spaced, in at least one, preferably several, second regions extending axially along the hollow fibers, so as to form one or more cavities at each second region between the shell and housing and connected through the housing wall to a fluid fitting.

Here, the essential core idea of the invention is that the internal volume of the compartment defined by the elastic shell can be enlarged and reduced because of the elasticity of the shell. The minimum volume of the chamber is reached when the elastic shell bears completely against the bundle of fibers due to its elasticity, particularly due to an independent return to that position or as a result of superatmospheric pressure in the chamber. In this way, the undesired occurrence of wall effects on the blood phase (the gap between the housing and the bundle of hollow fibers) can be prevented.

However, the internal volume of the chamber can be enlarged by pulling the elastic shell away from the bundle of hollow fibers.

According to the invention, this can be achieved by forming a cavity between the shell and the housing, particularly its inner housing wall in the at least one above-described second region, preferably in the several above-described second regions, that opens through the housing wall into a fluid connection, so that the cavity can be pressurized through this fluid connection is with a superatmospheric pressure against the internal pressure in the chamber and within the elastic shell, so that, as a result of this subatmospheric pressure in the cavity, the elastic shell is moved toward the cavity due to its elastic deformability and the internal chamber volume is thus enlarged. By enlargement of the chamber volume, the first fluid is therefore sucked into the chamber.

As mentioned previously in relation to a preferred application, the first fluid can be a patient's blood.

The advantage of the apparatus according to the invention therefore arises primarily from the fact that none of the patient's blood is needed to first fill a pump arranged outside of the blood circuit for the purpose of pumping. Nonetheless, the apparatus can also be operated with an external pump, for example a peristaltic pump.

The minimum blood volume of the apparatus is determined by the volume that is reached when the elastic shell lies completely against the bundle of fibers, whereas the maximum blood volume of the apparatus is determined when, as a result of subatmospheric pressure, the elastic shell has been completely pulled to the housing inner wall in the area of at least one second region that is at subatmospheric pressure.

In one possible embodiment, particularly one in which the apparatus is operated with an external pump, a provision can be made that two first regions are provided, each one being arranged on the axial end of the chamber and enclosing the chamber in the circumferential direction, the second region being arranged between these two first regions.

The axial regions here are the ends that delimit the chamber longitudinally of the hollow fibers. At these two opposite ends, the housing can lie annularly radially completely against the elastic either directly or via an intermediate element, thus surrounding the shell like a ring so that the shell cannot lift off the hollow fibers at these ends.

Between these two ends, the elastic shell is unsupported or out of contact with respect to the housing. Therefore, there is an at least annular cavity between the elastic shell and the housing inner wall between the axial ends. This at least one, preferably exactly one annular cavity forms a second region having a fluid connection in order to produce a pressure change in the annular cavity, thus changing the volume of the chamber.

In this embodiment, in one mode of operation the at least one second region or the cavity/annular cavity formed thereby is loaded via the fluid connection with periodic pressure pulses, the pressure pulses being in particular selected in the range, for example, from 10 to 120 or 30 to 60 pulses per minute in order to bring about a pumping of the first fluid through the chamber.

A provision can also be made to provide the pressure pulses with a first low number of pulses per minute, for example to make a selection in the range from 10 to 120 or 30 to 60 pulses per minute, with a second pressure pulse with a higher pulse frequency and lower amplitude, particularly 100 to 300 pulses per minute, being superposed over these first pressure pulses, so that pumping of the first fluid through the chamber is brought about as a result of the low-frequency pressure pulses, and a secondary flow/mixing of the first fluid in the chamber is brought about by the higher-frequency pulses.

Alternatively, with this embodiment of the apparatus in particular, the pressure pulsing can be selected in the range from 100 to 300 pulses per minute or even higher in order to bring about a secondary flow/mixing of the first fluid in the chamber, the first fluid [being delivered] through the chamber by a separate, particularly externally arranged pump, for example a peristaltic pump. In this variant, the apparatus is therefore operated merely as an oxygenator in the blood/oxygen application without an inherent pumping function.

In another embodiment of the apparatus, provision can be made that the housing inner wall contacts the shell in several first regions, each of which extends parallel to the hollow fibers, and the first and second regions surround the bundle of hollow fibers, particularly angularly equispaced.

Here as well, the same procedures can be used as those described above, it being preferred that the pumping function be performed by the apparatus itself, superposing the pressure pulses for the pumping function with higher-frequency pressure pulses of lesser amplitude.

Provision can be made here that the cavities are connected to a fluid connection through the housing wall not only in one of the second regions, but rather in several of the second regions, so that subatmospheric pressure, and hence an assist for the pumping function, can be achieved in several of the second regions. In particular, it is advantageous if the user has the ability to vary the quantity of the pumped volume when several fluid connections are present, namely by having one, two or several cavities of the several available be depressurized. This enables the maximum pumped volume to be varied between the single and n-fold volume of each cavity in a second region when a total of n cavities of a second region are provided with a fluid connection for depressurizing the apparatus according to the invention. Provision can preferably be made here that each cavity has equal volume.

In this context, it is regarded as being preferred if the first and second regions surround the bundle angularly equispaced. This design is preferred insofar as a uniform angular distribution enables the use of a symmetrical housing structure that can be manufactured without great technical complexity. Here, a respective first region can be disposed between two second regions and, likewise, a second region can be disposed between two first regions. The first and second regions can therefore be arranged alternatingly on the periphery.

For such a preferred embodiment, provision can be made, for example, that the bundle of hollow fibers has a substantially circular external cross section together with the surrounding shell perpendicular or at least transverse (at an inflow angle between 0° and 90°) to the hollow fibers.

In a first possible embodiment, the surrounding housing can be adapted to this cross section while having several recesses or offsets in the inner housing wall, preferably angularly equispaced, so that the shell does not lie against the inner housing wall in these regions. Such offsets or recesses can extend parallel to the hollow fibers. Each of these offset or recessed regions defines a cavity that is bounded in the direction toward the bundle by the shell and can lead through the housing wall to a fluid connection, particularly in order to depressurize or pressurize the cavity, thus moving, particularly sucking the elastic shell into the cavity.

In another embodiment, the housing can have a substantially polygonal free internal cross section, there being two regions formed between the corner areas of the housing inner wall and the shell in the hollow fibers. In terms of the invention, a cross section of the housing on the interior is deemed to be polygonal even if the corner areas are rounded, for example, so the polygonal cross section need not be understood as being polygonal in the strict mathematical sense. What is essential here is that flat surface areas of the housing inner wall be created between the corner areas with a polygonal cross sectional shape that merge together in the corner areas.

In a preferred embodiment of the apparatus, provision can be made with all possible housing variants that recesses/ holes are provided in two diametrically opposite second regions in the housing through which connections formed on the shell for the delivery and discharging of the first fluid through this housing wall pass. A one-way valve or an active valve can be arranged in at least one of the connections which permits flow of the first fluid in only one defined direction and thus functions as a check valve or corresponds to one.

For example, a hose piece can be formed in a single part for each of the inflow and outflow ports on the shell, which is made of an elastic material such as silicon, latex, or other blood-compatible material, these two hose pieces being diametrically opposite each other on the shell to ensure that the supplied and exhausted blood is conducted between the hollow fibers diametrically through the internal cross section of the shell in the direction transverse, preferably perpendicular to the fibers.

Accordingly, in the embodiment with an internal cross section of the housing with n corners which surrounds the shell, these delivery and discharge connections for the first fluid can be arranged in the area of two diametrically opposite corners of the cross section, so that a total of (n−2) second regions remain between the shell and the inner housing wall on which cavities are formed, particularly each of which can be provided with connections for depressurizing through the housing.

Thus, in an apparatus according to the invention with an internal cross section of the housing enclosing the shell with n corners, (n−2) increments of the volume delivered with a pump stroke can be achieved, each volume level corresponding to the volume that is enclosed in one of the second regions between the housing wall and the shell.

Thus, in a preferred embodiment with a housing design with n corners, as well as in housings with several recesses/ offsets in the second region, a provision can be made that, in two diametrically opposite, preferably all remaining second regions, the cavities formed between the shell and housing are provided with a fluid connection through the housing wall and can be depressurized, for example through an external vacuum pump.

The preferred embodiment can be selected here such that, particularly between the housing inner wall and the shell, an even number of second regions is embodied, particularly for which purpose the internal cross section of the housing perpendicular to the hollow fibers is polygonal with an even number of corners. This results in symmetry about the middle axis in the hollow fibers in which respective diametrically opposed second regions exist, two of which diametrically opposite regions can be used for the delivery and discharging of the first fluid, and the remaining, diametrically opposite areas can be used for depressurizing in order to achieve the desired pumping function.

In order to ensure that the shell tightly contacts the housing inner wall in the first regions and that the individual volumes in the respective second areas are separated from each other, provision can be made that the shell is or can be rigidly connected to the housing inner wall in these first regions.

In a preferred embodiment, this can be achieved by providing projections in the first regions on the shell extending parallel to the hollow fibers, each projection lying in or locking into a groove extending in the housing inner wall parallel to the hollow fibers. By virtue of the positive axially extending connection between the projection and groove, a seal is achieved between the outside of the shell and the inside of the inner housing wall, so that no leakage of fluid is possible between adjacent second regions and each cavity formed in a second region between the housing inner wall and shell can thus be separately and individually depressurized.

For assembly, provision can be made here that each of the above-described projections extending parallel to the hollow fibers is pushed in the hollow fibers into the groove on the housing inner wall, particularly during assembly in which the entire arrangement of bundle and shell is pushed axially into the rigid housing.

The design of the groove can be such that the groove opening has a smaller width in the direction toward the shell than the interior of the groove, so that a commensurately embodied projection on the outside of the shell near the shell surface has a smaller width than at a greater distance from the shell surface. For example, the groove cross section and the projection cross section can be circular or even triangular perpendicular to the hollow fibers, so that a projection pushed into the corresponding groove is held radially securely in the groove and seated in a sealing manner therein.

In another preferred modification of the apparatus according to the invention, provision can also be made that the bundle of hollow fibers is wound on a core. Such a core can be provided, for one, to stabilize the bundle of hollow fibers and, for another, have a hollow design in an apparatus according to the invention where the external core wall facing toward the bundle has openings toward the hollow core interior that are sealed/covered by a flexible membrane and the core interior has a fluid connection, is particularly depressurizable via the core interior in the same manner as the above-mentioned individual cavities in the second regions between the shell and housing inner wall.

With this embodiment, the possibility also exists of supporting the pumping function by pressurizing or depressurizing the core interior to move the flexible membrane that seals the core openings into the interior of the core, thus also enlarging the effective volume of the apparatus.

Provision can be made here that the core has a polygonal external cross section perpendicular to the hollow fibers, with holes in the flat surface areas between the edges of the core running parallel to the hollow fibers. Here, the number of corners of the core preferably corresponds to the number of corners of the housing.

In such a hollow core, independently of its external cross section that can optionally also be round, the core can carry a flexible elastic shell that covers the openings of the core. Such a shell can be formed, for example, by a hose that lies tightly against the core surface.

A preferred illustrated embodiment of the invention is described in the FIGS. below.

Figure 1:
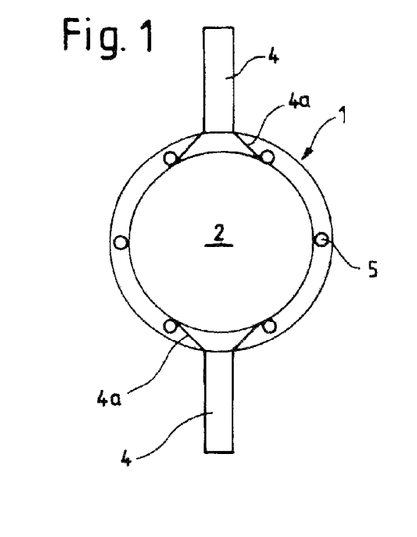
FIG. 1 is a section through the chamber for conducting the first fluid perpendicular to the direction of the hollow fibers.
Figure 2:
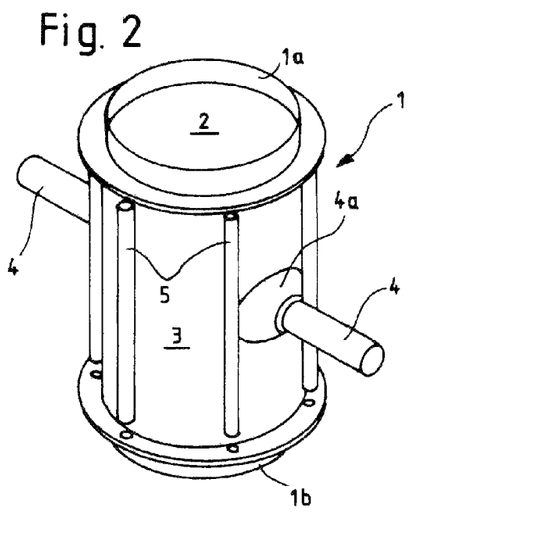
FIG. 2 is a perspective view of the same chamber.

FIGS. 1 and 2 are two different views of the chamber 1 of an apparatus according to the invention in which is held a bundle of hollow fibers not illustrated in FIGS. 1 and 2.

As shown in FIG. 1, the bundle of hollow fibers is located in an interior 2 of the chamber 1, with the hollow fibers extending perpendicular to the drawing plane in FIG. 1.

With reference to FIGS. 1 and 2, the chamber 1 has a substantially cylindrical shape with a substantially circular cross section perpendicular to the axial extension of the hollow fibers. The chamber 1 here has axial ends 1a and 1b and an elastic shell 3 extending between these axial ends that, due to its elasticity and hence its tendency to contract, bears radially against the outside of the bundle of hollow fibers. This shell 3 surrounds the bundle completely. The axial ends 1a and 1b can be mounted on the shell 3 at a later point in time, for example molded on so as to be sealed thereto, for example adhesively joined after the shell 3 was been inserted into a housing while holding the bundle.

The axial ends of the hollow fibers not shown in FIGS. 1 and 2 terminate in a sealed manner on the transverse planes of the two axial ends 1a and 1b of the chamber 1, so that the individual hollow fibers can be charged through these axial ends 1a and 1b with a fluid that is then conducted axially parallel to and through the hollow fibers.

It can also be seen here that connections 4 for the delivery and discharging of the first fluid are provided on the elastic shell extending perpendicular to the axial extension of the hollow fibers. Here, these connections 4 can be embodied, for example, as hose fittings that are formed unitarily with the flexible shell 3. Accordingly, the connections 4 can be formed from the same elastic material as the shell 3 itself.

With reference to FIGS. 1 and 2, it is therefore clear that the first fluid can be conducted through the chamber 1 (shown here) in a direction perpendicular to the hollow fibers. Within at least one of the connections 4, particularly in the region near the shell 3, a one-way valve can be provided, for example, in order to define a direction of flow. The flexible transition region 4a between a connection 4 and the shell 3 can serve as a collapsible reservoir.

FIGS. 1 and 2 also show how several projections 5 are provided on the outer surface of the shell 3 each extending parallel to the hollow fibers and angularly equispaced around the shell 3. In a preferred embodiment, the projections 5 extend the entire axial length between the ends 1a and 1b.

Figures 3, 4:
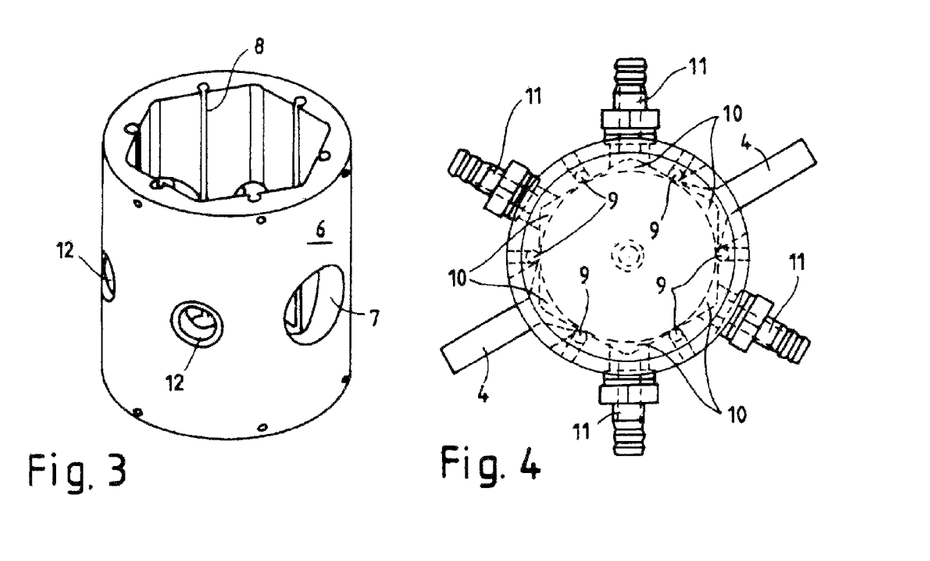
FIG. 3 is the housing of an apparatus according to the invention with a polygonal internal cross section.
FIG. 4 is a sectional view of the overall apparatus according to the invention perpendicular to the extension of the hollow fibers.

FIG. 3 shows the only illustration of the housing of an apparatus according to the invention, which housing serves to hold on its interior the chamber 1 formed by the elastic shell 3 and the bundle of hollow fibers therein, as shown in FIGS. 1 and 2. The connections 4 for delivery and discharging of the first fluid can extend through holes 7 in the housing 6 that are diametrically opposite each other.

The chamber 1, as shown in FIGS. 1 and 2, can be inserted here into the internal space of polygonal cross section defined by the housing 6 axially of the hollow fibers, with the projections 5 fitting into radially inwardly open and axially extending grooves 8 in the inner wall of the housing 6. For this purpose, the grooves 8 and the projections 5 have complementary cross sections seen perpendicular [parallel] to the hollow fibers.

With reference to FIG. 4, the shell 3 lies against the here cross-sectionally hexagonal housing inner wall in first regions 9, the seal between the shell and the housing inner wall being achieved here through the positive connection between the projections 5 and the grooves 8.

The first regions 9 delimit second regions 10, also angularly equispaced, in which the elastic shell 3 bearing against the hollow fibers is spaced from the housing inner wall, thus resulting in cavities in these second regions 10 between the circular external cross section of the shell and the n-sided—here hexagonal—internal cross section of the housing 6. The individual cavities formed in the second regions 10 are sealed off from one other by the tight positive connection of the projections 5 and grooves 8.

Here, FIG. 4 shows that the diametrically opposite holes 7 of the housing 6 open into two diametrically opposite second regions, the input and output fittings 4 for supplying and withdrawing the first fluid extending through the housing.

In all the remaining second regions 10, the cavities formed in these second regions 10 are connected to fluid fittings 11 through which each of the individual cavities can be depressurized and/or pressurized individually or even several together and simultaneously, thus making it possible to move the shell 3 that surrounds the bundle of hollow fibers toward the housing inner wall in the respective second region 10 when depressurized, thus enlarging the volume of the chamber 1. As a result of such enlargement, blood is sucked through the inlet connection 4 into the chamber, at least one one-way valve in the inlet or outlet 4 ensuring that blood moves in a predetermined direction.

If depressurization is relieved or if superatmospheric pressure is applied, then the shell 3 returns to its starting position and bears against the outside of the bundle of fibers, thus reducing the internal volume of the chamber 3 and pumping the first fluid through the output connection 4 from the chamber.

The fluid fittings 11 shown here can be mounted in the housing in holes provided for this purpose; for example, they can be screwed into these holes 12 so as to seal.

Figures 5, 6, 7:
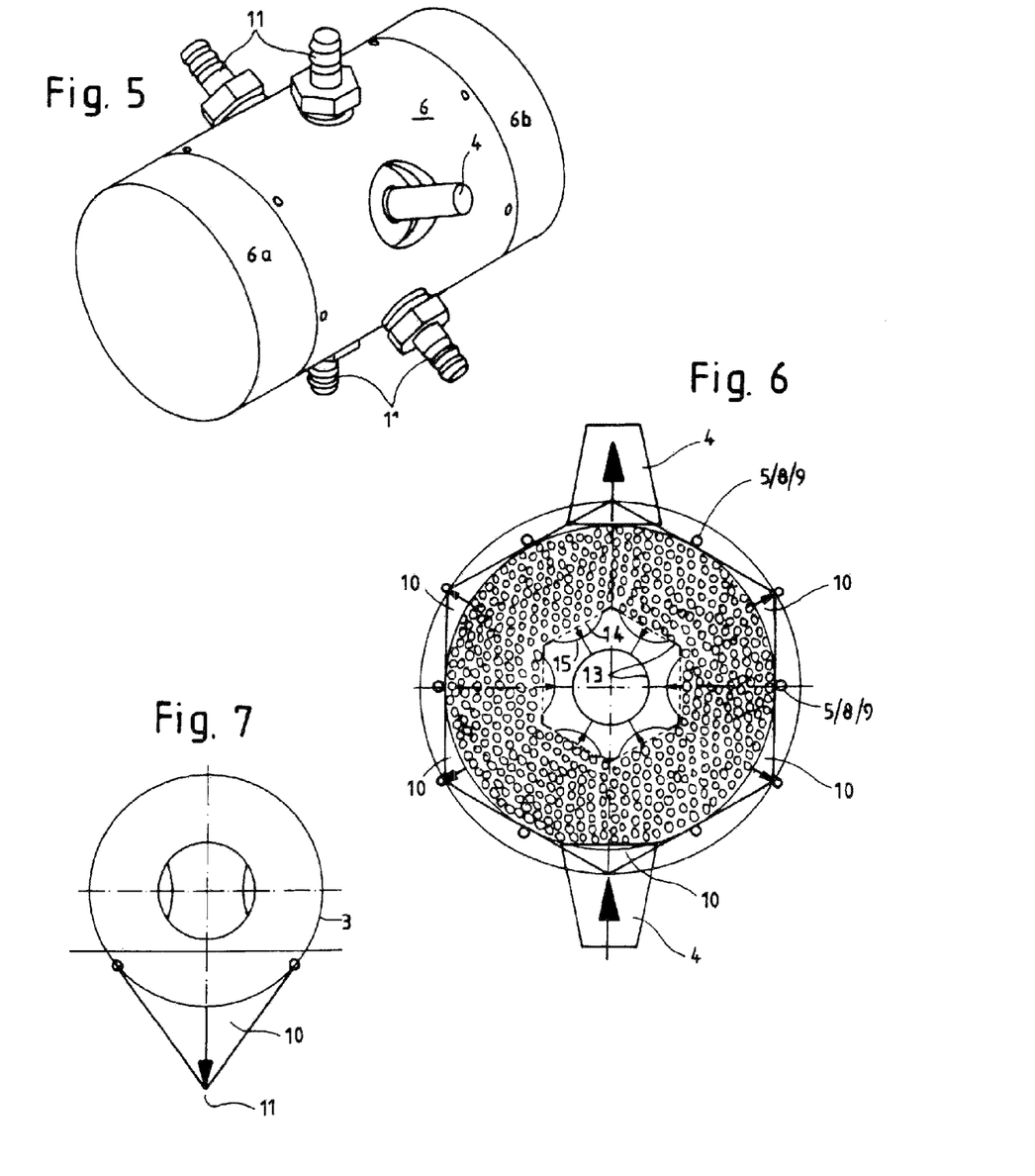
FIG. 5 is a perspective view of the overall apparatus according to the invention.
FIG. 6 is a side view perpendicular to the extension of hollow fibers with a likewise hollow core region for assisting the pumping function.
FIG. 7 shows the expansion of the shell within a second region.

FIG. 5 shows a perspective view of FIG. 4 showing caps 6a and 6b are attached to both axial ends of the housing 6 through which charging of the bundle of hollow fibers arranged in the housing 6 can occur with the second fluid. The relevant fluid connections are not shown in FIG. 5.

This results in the additional advantage here that the chamber 1 and hence the bundle of fibers can be removed from the housing 6 after use with the surrounding elastic shell 3 and a new chamber 1 inserted. Accordingly, a large portion of the apparatus according to the invention can be reused, it being possible to exchange, for reasons of hygiene, only the portion conducting the first fluid, particularly when the apparatus is used in a medical field.

FIG. 6 is a cross section corresponding substantially to FIG. 4 but showing the bundle of fibers here wound on an inner core 13 that is also formed in this nonetheless non-restricting embodiment with n sides (n=6). The flat surface areas present between the individual external corners of the core have form cavities 14 that are sealed and/or covered by an elastic membrane 15.

In one embodiment, this membrane 15 can extend as a shell or as a hose over the entire axial length of the core 13 and is therefore located between the core 13 and the bundle of fibers. The interior of the tubular core 13 can also be pressurized and/or depressurized through a connection that is not shown here separately, thus enabling the membrane 15 to be moved, as shown here, into the inner cavities of the core 13, thus enlarging the chamber volume in the same manner as depressurization via the connections 11.

The configuration of a hollow core with cavities that are sealed by an elastic membrane or shell can therefore be used for assisting the pumping function in the same manner as the subatmospheric pressure applied via the connections 11, thus making it possible to determine the volume pumped in one stroke by the number connections that are used for depressurization. What is more, provision can be made to apply phase-shifted subatmospheric pressure control of the individual connections in order to successively deliver a predefined volume of blood through successive depressurization of the connections 11 or of the inner core.

Figure 8:
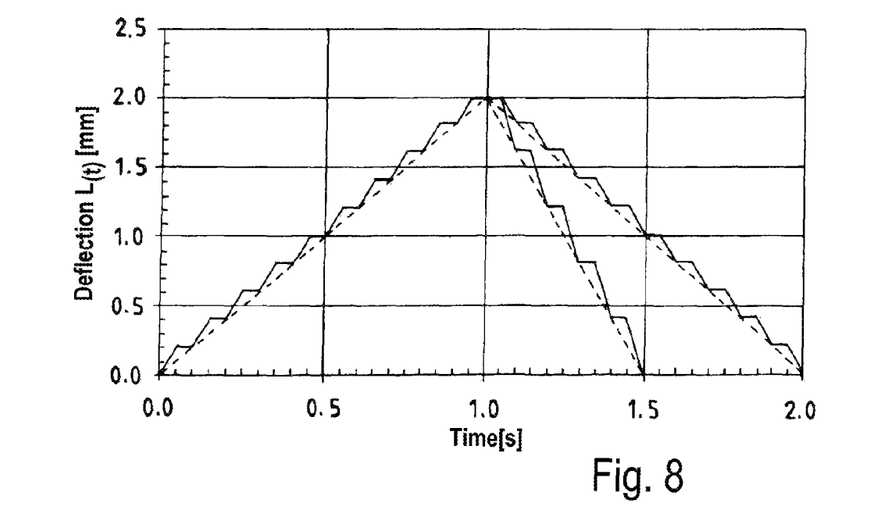
FIG. 8 is the curve with respect to time of the expansion that can be achieved by control.

In conjunction with FIG. 8, FIG. 7 shows the possibilities for variable control of the time profile of the deflection L of the shell 3 at the site of the second regions 10 toward a housing corner/edge. The time profile in the expansion L of the shell 3 at this location in the direction of the connections 11 is an important parameter for the generation of the flow of the first fluid, here particularly blood, in the volume of the chamber 1 and therefore has substantial influence, particularly in an application as an oxygenator, on the mass transfer between the two fluids, here particularly from gas to the blood.

A provision can be made here, as shown in FIG. 8, that the timing for sucking and therefore for generating the subatmospheric pressure in the cavity in the region 10 is set up differently compared to the timing for increasing and decreasing pressure in order to bring about the return of the membrane 3 to lie against the hollow fibers. It is both possible for the time profile of the deflection of the membrane and hence the volume change to be linear during the sucking or pressing, as FIG. 8 shows with the broken lines, and for it to be substantially sawtooth-shaped with different, adjustable edge angles. These different adjustments can be made particularly by varying the application of the subatmospheric/superatmospheric pressures via the connections 11 or also the internal connection if a hollow core is provided. The type and time profile of the flow of the first fluid, here particularly blood, can therefore be influenced in a targeted manner.

Another substantial advantage of the inventive apparatus illustrated here is that it can be especially small, and can have a small fill volume to enable it to be used in infants and premature babies or small animals. For example, the fill volume can be set at less than 100 milliliters, preferably less than 50 milliliters, especially preferably smaller than 30 milliliters, particularly in order to offer extracorporeal lung support in infants and premature babies.

With particular reference to FIGS. 1 and 2, silicon is used as a material for the hollow fibers and/or the shell 3. Provision can be made here to manufacture the shell, the connections 4, and the connections and seals to the bundle of hollow fibers at the axial ends from a casting. A provision can be made to pull the cover 6a and bottom 6b of the housing body 6 in a sealed manner over the axial ends 1a and 1b of the inner chamber 1, thus making it unnecessary to adhesively seal the individual components to each other and enabling reuse of the external housing components.

Figure 9:
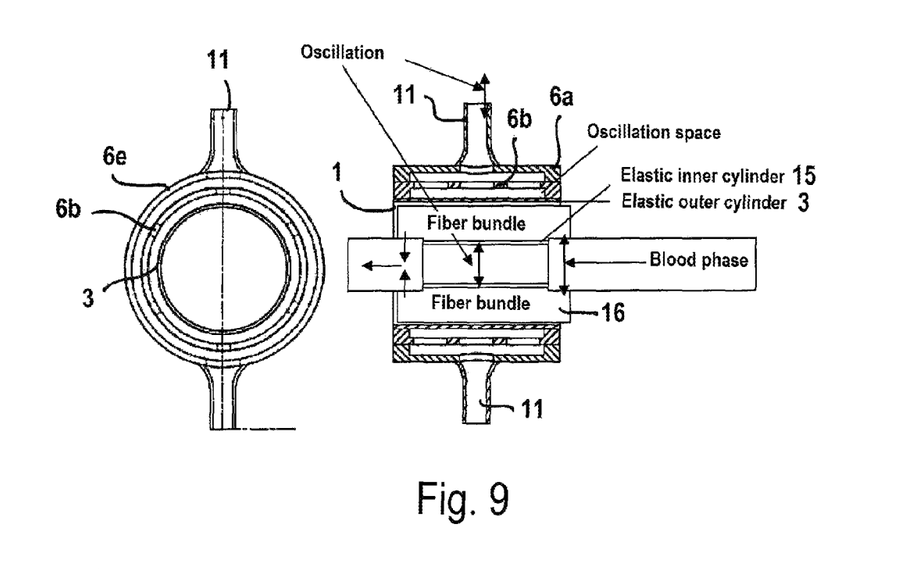
FIG. 9 shows an embodiment with axial end-side contact in two first regions and a second region/annular cavity arranged between them.

FIG. 9 shows an embodiment of the device in which the elastic shell 3 is contacted annularly at the two axial ends of the bundle of hollow fibers 16 by the housing that is constructed in two parts. These axial ends thus form two first regions.

Between these axial ends, the housing is out of contact with the elastic shell 3, so that it can be pulled from the bundle of fibers 16 by subatmospheric pressure applied to the fluid connection 11 that leads to the second region/annular cavity. This changes the volume of the chamber 1 surrounded the shell 3.

The housing enclosing the shell 3 is constructed here of two radially joined parts, for example components 6a and 6b form a cylindrical element with holes/openings. It can form a stop for the shell 3, thus limiting the enlargement of the volume, for example when the total volume between the housing and shell 3 is greater than needed. This also ensures that the shell cannot seal the fluid connection 11 when the shell expands.

In this embodiment, the blood or any fluid can be pumped through the chamber 1 by connections (not shown here), for example, with an external pump (not shown), such as for example a peristaltic pump. In this case, the apparatus does not perform a pumping function. The blood can flow as described above between the connections, for example transverse to the bundle of hollow fibers, which is to say substantially radially to the axially extending hollow fibers. However, it is also possible to allow the blood to flow parallel to the hollow fibers.

Through at least one of the fluid connections 11, a pressure oscillation/pulsation is also applied during operation of the apparatus, the pressure oscillations ranging, for example, from 100 to 300 oscillations per minute, or even higher.

The pressure oscillations are transferred through the elastic shell to the pumped blood to create secondary flows, thus improving the mixing of the blood and promoting contact with the permeable hollow fibers, thus improving, in turn, the mass transfer. This is true independent of the pairing of two mass-exchanging fluids and not only to blood/oxygen.

The invention claimed is:

1. An apparatus for exchanging mass and/or energy between first and second fluids, the apparatus comprising:
   an elastic shell forming a chamber through which the first fluid flows;
   a bundle of mass- or energy-permeable fibers extending in the shell transversely to the direction of flow of the first fluid and through which the second fluid can flow and the first fluid cannot flow;
   a rigid housing around the elastic shell having an inner wall that contacts the elastic shell in several first regions angularly equispaced around the bundle and from which the elastic shell is spaced at several second regions toward the hollow fibers, the first regions extending parallel to the hollow fibers, the second regions being angularly eguispaced around the bundle and forming between the shell and the housing at least one cavity; and
   a fluid connection opening into the cavity through the housing.

2. The apparatus as set forth in claim 1, wherein two of the first regions are provided at a respective axial end of the chamber and circumferentially enclosing the chamber with the second regions between these two first regions.

3. The apparatus as set forth in claim 1, wherein the bundle and the shell have a substantially circular external cross section and the surrounding housing is of similar cross section and has in its inner housing wall several angularly equispaced recesses or offsets that form respective second regions.

4. The apparatus as set forth in claim 1, wherein the bundle and the shell have substantially circular external cross sections and the housing inner wall has a substantially polygonal internal cross section, the second regions being formed between corners of the housing inner wall and the shell and extending parallel to the hollow fibers.

5. The apparatus as set forth in claim 1, wherein the connections open into two diametrally opposite second region and serve for supplying and withdrawing the first fluid through the housing inner wall to the respective cavities, the apparatus further comprising:
a one-way valve in at least one of the connections.

6. The apparatus as set forth in claim 5, wherein the cavities in the two diametrally opposite second regions are formed between the shell and housing are connected through the housing wall via the respective fluid connections that can be at subatmospheric and/or superatmospheric pressure.

7. The apparatus as set forth in claim 1, wherein an even number of the second regions is formed between the housing inner wall and the shell, an internal cross section of the housing perpendicular to the hollow fibers being polygonal with an even number of corners.

8. The apparatus defined in claim 1, further comprising:
means for pressurizing and depressurizing the cavity via the connections and thereby compressing and decompressing the bundle.

9. The apparatus defined in claim 8, further comprising:
a check valve in one of the connections for permitting flow of the second fluid only in one direction transversely through the bundle between the fibers, whereby alternate pressurization and depressurization of the cavity pumps the second fluid transversely through the bundle between the fibers.

10. The apparatus defined in claim 8, wherein the inner surface of the housing is of polygonal cross section with radially inwardly projecting and longitudinally extending corners, a plurality of the second regions being formed between the corners.

11. The apparatus defined in claim 8, wherein the elastic shell is anchored to the inner surface of the housing to each side of the second region.

12. The apparatus defined in claim 8, wherein the means for pressurizing and depressurizing the cavity includes at least one of the connections.

13. An apparatus for exchanging mass and/or energy between first and second fluids, the apparatus comprising:
an elastic shell forming a chamber through which the first fluid flows;
a bundle of mass- or energy-permeable fibers extending in the shell transversely to the direction of flow of the first fluid and through which the second fluid can flow and the first fluid cannot flow;
a rigid housing around the elastic shell having an inner wall that contacts the elastic shell in several first regions and from which the elastic shell is spaced in at least one second region toward the hollow fibers, the second region forming between the shell and the housing at least one cavity;
a fluid connection opening into the cavity through the housing; and
projections extending on the shell parallel to the hollow fibers in the first regions and each fitting in a positive manner in a respective groove extending in the housing inner wall parallel to the hollow fibers.

14. An apparatus for exchanging mass and/or energy between first and second fluids, the apparatus comprising:
an elastic shell forming a chamber through which the first fluid flows;
a bundle of mass- or energy-permeable fibers wound on a hollow core and extending in the shell transversely to the direction of flow of the first fluid and through which the second fluid can flow and the first fluid cannot flow, the core having an outer surface facing toward the bundle and openings to the hollow core interior at least in areas that are sealed/covered by a flexible membrane;
a fluid connection opening into an interior of the core and via which the core interior can be pressurized or depressurized;
a rigid housing around the elastic shell having an inner wall that contacts the elastic shell in several first regions and from which the elastic shell is spaced in at least one second region toward the hollow fibers, the second region forming between the shell and the housing at least one cavity; and
a fluid connection opening into the cavity through the housing.

15. An apparatus for exchanging mass and/or energy between first and second fluids, the apparatus comprising:
an elastic shell forming a chamber through which the first fluid flows;
a bundle of mass- or energy-permeable fibers wound on a hollow core and extending in the shell transversely to the direction of flow of the first fluid and through which the second fluid can flow and the first fluid cannot flow, the core having a polygonal outside cross section perpendicular to the hollow fibers, openings being formed in flat surface areas between edges of the core that extend parallel to the hollow fibers, the core having a number of corners on its cross section that is the same as that of the housing;
a rigid housing around the elastic shell having an inner wall that contacts the elastic shell in several first regions and from which the elastic shell is spaced in at least one second region toward the hollow fibers, the second region forming between the shell and the housing at least one cavity; and
a fluid connection opening into the cavity through the housing.

16. The apparatus as set forth in claim 15, wherein the core is formed by a flexible elastic shell.

17. A The method as set forth in of operating an apparatus for exchanging mass and/or energy between first and second fluids, the apparatus comprising:
an elastic shell forming a chamber through which the first fluid flows;
a bundle of mass- or energy-permeable fibers extending in the shell transversely to the direction of flow of the first fluid and through which the second fluid can flow and the first fluid cannot flow;
a rigid housing around the elastic shell having an inner wall that contacts the elastic shell in several first regions and from which the elastic shell is spaced in at least one second region toward the hollow fibers, the second region forming between the shell and the housing at least one cavity; and
a fluid connection opening into the cavity through the housing and through which the cavity is pressurizable with periodic pulses,
the method comprising the steps of:
setting the pressure pulses
a) in the range from 10 to 120 pulses per minute in order to pump the first fluid through the chamber or to assist heart function, or b) with a first low number of pulses per minute in the range from 10 to 120 pulses per minute, with a second pressure pulse of a higher number of pulses per minute and a lower amplitude 100 to 300 pulses per minute, being superposed over these pressure pulses, thus pumping the first fluid through the chamber with the low-frequency pulses, and a secondary flow/mixing of the first fluid in the chamber being brought about as a result of the higher-frequency pulses, or c) in the range of greater than 100 pulses per minute in order to bring about a secondary flow/mixing of the first fluid in the chamber, the first fluid being pumped through the chamber by a separate externally arranged pump.

* * * * *